(12) United States Patent
Auguste et al.

(10) Patent No.: US 6,338,839 B1
(45) Date of Patent: Jan. 15, 2002

(54) TRANSFER-RESISTANT MAKE-UP OR CARE COMPOSITION CONTAINING A VOLATILE LINEAR SILICONE

(75) Inventors: Frédéric Auguste, Chevilly-Larue; Pascal Arnaud, 1'Hay-les-Roses; Jean-Yves Fouron, Bourg-la-Reine, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/371,531

(22) Filed: Aug. 10, 1999

(30) Foreign Application Priority Data

Aug. 10, 1998 (FR) .............................. 98 10256
Sep. 4, 1998 (FR) ............................. 98 11065

(51) Int. Cl.$^7$ ...................... A61K 7/025; A61K 7/031; A61K 7/00; A61K 9/00; A61K 7/06
(52) U.S. Cl. ...................... 424/64; 424/70.7; 424/401; 424/485; 424/DIG. 5; 424/400; 424/70.11; 424/63; 424/69; 514/844; 514/937
(58) Field of Search .............................. 424/DIG. 5, 64, 424/400, 59, 61, 70.7, 401, 485, 70.1, 63, 69; 514/844, 937

(56) References Cited

U.S. PATENT DOCUMENTS 5,505,937 A * 4/1996 Castrogiovanni et al. ...... 424/64
5,738,841 A * 4/1998 Mellul et al. .................. 424/59
5,746,945 A 5/1998 Ryklin et al.

FOREIGN PATENT DOCUMENTS

| EP | 0 400 546 | 12/1990 |
|---|---|---|
| EP | 0 440 542 | 8/1991 |
| FR | 2 771 003 | 5/1999 |
| GB | 2 259 015 | 3/1993 |

OTHER PUBLICATIONS

Masashi Yoshida et al., "Water–Resistant And Oil–Resistant Cosmetic Makeups", Chemical Abstracts, XP–002104174, An 125:158787 & JP 08 143 426, Jun. 4, 1996.

* cited by examiner

Primary Examiner—Diana Dudash
Assistant Examiner—Clinton Ostrup
(74) Attorney, Agent, or Firm—Oblon, Spivak, McClelland, Maier & Neustadt, P.C.

(57) ABSTRACT

A transfer-resistant make-up or care composition, comprising:
  a fatty phase, and
  a volatile solvent comprising a linear decamethyltetrasiloxane and at least one additional solvent which has an evaporation speed that is greater than the evaporation speed of the linear decamethyltetrasiloxane.

22 Claims, No Drawings

TRANSFER-RESISTANT MAKE-UP OR CARE COMPOSITION CONTAINING A VOLATILE LINEAR SILICONE

FIELD OF THE INVENTION

1. Field of the Invention

The present invention relates to a transfer-resistant make-up or care composition for the skin, superficial body growths (nails, eyelashes, eyebrows) or the lips, containing a combination of a volatile linear silicone, decamethyltetrasiloxane, and at least one other solvent which more volatile than the silicone. The invention also relates to the use of a combination of a volatile linear silicone and at least one other solvent which is more volatile than the first solvent, as a volatile phase in transfer-resistant make-up or care products for the skin, superficial body growths (nails, eyelashes, eyebrows) or the lips, to a process for preparing such transfer-resistant make-up or care products and to a process for limiting the transfer of a make-up and care composition for the skin, superficial body growths or the lips.

2. Background of the Invention

The development of so-called "transfer resistant" make-up products is currently the subject of considerable cosmetic research. These products, for example foundations, lipsticks, eye shadows or face powders, axe distinguished by the fact that once they have been applied to the skin or the lips, they do not become appreciably deposited on surfaces with which they come into contact (glass, cup, cigarette or clothing, for example).

The first approach for preventing the transfer of applied cosmetic products involves coating them with a layer of products which are renowned for their anti adhesive properties, such as fluoro products or silicone products. However, formulations of this type have the drawback of being relatively unsuitable for cosmetic use. For example, the film of lipstick becomes oily and liable to migrate onto the skin adjacent to the lips and the eyelids.

Another possibility for obtaining transfer resistant products involves using silicone polymers or resins in combination with volatile starting materials which, after evaporation of the latter, leave an inert film which is resistant to transfer onto other surfaces. The volatile starting materials used are, conventionally, cyclic silicones of very low viscosity (less than 3 centistokes) or isoparaffins.

Many transfer-resistant cosmetic formulations, in particular lipsticks and foundations, currently use the cyclic volatile silicone cyclotetradimethyl siloxane, also known as cyclomethicone $D_4$, or $D_4$, for short, as the main volatile solvent.

This cyclic silicone, generally used in combination with isoparaffins and in particular with isododecane, gives the compositions excellent cosmetic and physicochemical properties (good spreading, nongreasy feel, compatibility with the other constituents of the formulation, suitable speed of evaporation, etc.). However, it has the major and sometimes prohibitive drawback of having an excessively high crystallization temperature. Specifically, since its crystallization point is about 18° C., crystallization phenomena can arise at the surface of make-up compositions when they are stored at low temperature.

SUMMARY OF THE INVENTION

An object of the present invention was to find a volatile solvent or a combination of volatile solvents whose chemical and physicochemical properties are comparable to those of cyclomethicone $D_4$, but whose crystallization temperature is markedly lower than room temperature, thus avoiding the crystallization phenomena described above.

The Inventors have now found that it is possible to replace the volatile silicone cyclomethicone $D_4$ in transfer-resistant make-up or care compositions with a combination of linear silicone, namely decamethyltetrasiloxane, also known as $L_4$, and another cosmetic solvent which is more volatile than the linear silicone $L_4$. These transfer-resistant cosmetic compositions using the linear silicone $L_4$ and another solvent which is more volatile than the latter, as volatile solvents for the fatty phase, conserve the advantageous cosmetic properties, such as the non-greasy feel characteristic of transfer-resistant products, a sufficiently fast evaporation speed and easy, homogeneous spreading.

Accordingly, the object of the invention, and others, may be accomplished with a transfer-resistant make-up or care composition comprising, as volatile solvents for a fatty phase, the combination of linear decamethyltetrasiloxane ($L_4$) and at least one second solvent which is more volatile than linear decamethyltetrasiloxane $L_4$.

The object of the invention may also be accomplished with the use of the combination of $L_4$ and at least one second solvent which is more volatile than $L_4$, to give non-transfer properties to make-up or care compositions.

The object of the invention may also be accomplished with a process for preparing transfer-resistant make-up compositions.

Also, the object of the invention may also be accomplished a process for limiting the transfer of a make-up or care composition from the skin, superficial body growths or the lips onto a surface with which the skin, the superficial body growths or the lips come into contact, this process consisting in introducing a combination of a volatile linear silicone and another volatile solvent whose evaporation speed is greater than that of the silicone and as defined above, into the composition.

A more complete appreciation of the invention and many of the attendant advantages thereof will be readily obtained as the same becomes better understood by reference to the following detailed description.

DETAILED DESCRIPTION OF THE INVENTION

The search for a compound or a mixture of compounds to replace cyclomethicone $D_4$, which have comparable volatility to that of the latter compound, required the development of a reliable method for evaluating the evaporation speeds of cosmetic solvents.

The evaporation speeds may be determined in the following way:

15 g of the solvent or of the mixture of solvents to be tested are introduced into a crystallizing dish (diameter: 7 cm) in a temperature-controlled (25° C.) and hygrometry-controlled (50% relative humidity) chamber. The liquid is left to evaporate freely, without stirring it, while providing ventilation by means of a ventilator (SEMI rotating at 2700 rpm) placed 20 cm above the crystallizing dish containing the solvent. The mass of solvent remaining in the crystallizing dish is measured at regular intervals. The evaporation speeds are expressed as mg of solvent evaporated per unit of surface area ($cm^2$) and per unit of time "minute").

The linear volatile silicone $L_4$ used in the present invention as volatile solvent to replace cyclomethicone $D_4$ is a tetramer of dimethylsiloxy units ending with methyl groups.

It has a crystallization point of −68° C., a viscosity of less than 3 centistokes and an evaporation speed, measured under the conditions described above, equal to 0.309 mg/cm²/minute. Such a silicone is sold, for example, by Dow Corning under the name DC 200 Fluid 1.5 cSt.

Since this silicone has a markedly lower evaporation speed than that of cyclomethicone $D_4$, which is 0.626 mg/cm²/minute, it is preferably used in combination with at least one second solvent having an evaporation speed at least equal to 0.70 mg/cm²/minute, and preferably not exceeding 7.0 mg/cm²/minute.

Examples of such physiologically acceptable second volatile solvents include linear or branched alkanes, cyoloalkanes, fluorohydrocarbons, silicones or modified silicones, and mixtures thereof. Among the preferred volatile solvents are 2,2,4,4,6-pentamethylheptane (isododecane) and the mixture of isoparaffins sold under the name Isopar E® by Exxon Chemical.

In one preferred embodiment, the second volatile solvent used is the isododecane of formula:

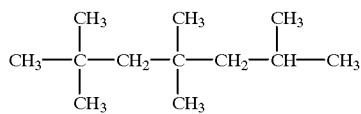

This compound is sold, for example, under the name Permethyl® 99A by Presperse Inc. Under the measurement conditions specified above, its evaporation speed is equal to 0.803 mg/cm²/minute.

Other second volatile solvents which may be used are linear octamethyltrisilaxane ($L_3$), which has an evaporation speed of 2.34 mg/cm²/minute, and hexamethyldisiloxane ($L_2$). When the volatile second solvent is octamethyltrisilaxane, it is present such that the octamethyltrisiloxane/decamethyltetrasiloxane weight ratio is less than 0.4.

The respective proportions of decamethyltetrasiloxane and of the volatile second solvent depend mainly on the evaporation speed of this second solvent. The higher this evaporation speed, the larger the proportion of decamethyltetrasiloxane.

Thus,
when the evaporation speed of the second solvent, measured under the conditions described above, is between 0.70 and 0.90 mg/cm²/minute, preferably between 0.75 and 0.85 mg/cm²/minute, in other words when the ratio of the evaporation speed of the volatile second solvent to that of the decamethyltetrasiloxane is between 2.2 and 3, preferably between 2.4 and 2.8, the decamethyltetrasiloxane is used in a proportion of from 15 to 40% by weight (inclusive of all specific values and subranges therebetween, including 20, 25, 30 and 35% by weight), preferably in a proportion of from 25 to 35% by weight, relative to the total weight of the mixture of volatile solvents; and when the evaporation speed of the second solvent, measured under the conditions described above, is between 4.0 and 7.0 mg/cr²/minute, preferably between 5.0 and 6.0 mg/cm²/minute, in other words when the ratio of the evaporation speed of the volatile second solvent to that of the decamethyltetrasiloxane is between 12.9 and 22.7, preferably between 16.1 and 19.5, the decamethyltetrasiloxane is used in a proportion of from 75 to 95% by weight (inclusive of all specific values and subranges therebetween, including 80, 85 and 90% by weight), preferably in a proportion of from 85 to 95% by weight, relative to the total weight of the mixture of volatile solvents.

In the case of mixtures of solvents containing, besides $L_4$, two or more other more volatile solvents, the proportion of more volatile solvents is generally lower the higher the evaporation speed of the mixture they form. Among the preferred ternary mixtures, examples include $L_4$/isododecane/Isopar E® mixtures (Isopar E® is a mixture of isoparaffins sold by the company Exxon Chemical), in particular the mixture, as a weight percentage, of 91% $L_4$/6% Isopar E®/3% isododecane. Other examples include $L_4$/isododecane/$L_3$ ternary mixtures for which the $L_3/L_4$ weight ratio is less than 0.4.

The make-up or care compositions of the present invention can also contain one or more waxes of animal, plant or synthetic origin having a melting point of greater than 30° C. and ideally greater than 45° C. These waxes generally act as hardeners and/or gelling agents. They are chosen, inter alia, from optionally hydrogenated, hydroxylated or acetylated lanolin, beeswax, spermacety, lanolin alcohols, lanolin fatty acids and acetylated lanolin alcohol, carnauba wax, candelilla wax, kapok wax, Ouricury wax, rice wax, hydrogenated jojoba wax, alfalfa wax, Japan wax, cork fiber wax or sugarcane wax, cocoa butter, paraffin wax, lignite wax, petrolatum wax, petroleum jelly wax or microcrystalline waxes, ceresin, ozokerite, montan wax, polyethylene waxes, the waxes obtained by FischerTropsch synthesis, linear esters resulting from the action of a saturated $C_{10-40}$ carboxylic acid and a saturated $C_{40-10}$ alcohol, $C_{20-60}$ fatty alcohols, cetyl alcohol, stearyl alcohol, calcium lanolates or stearates and hydrogenated castor, palm, coconut, sunflower or copra oil.

The compositions of the present invention can also contain at least one silicone gum, also contain at least one silicone gum, i.e., polysiloxanes with a high number-average molecular mass, ranging from 200,000 to 1,000,000, and having a viscosity of greater than 500,000 mPa·s.

The amount of silicone gum is generally less than 2% by weight and preferably equal to 0.1% by weight. This range includes all specific values and subranges therebetween, such as 0.01, 0.02, 0.05, 0.2, 0.5, 1.0 and 1.5% by weight.

The transfer-resistant cosmetic compositions can also comprise at least one non-volatile oil of plant, animal, mineral or synthetic origin. Specific examples include for example:

silicone oils of low viscosity, such as linear polysiloxanes with a degree of polymerization of between 3 and 2000, for example polydimethylsiloxanes with a viscosity of greater than 10 mPa·s, phenyldimethicones, phenyltrimethicones and polyphenylmethylsiloxanes, and mixtures thereof;

hydrocarbon-based oils such as perhydrosqualene liquid triglycerides of $C_{4-10}$ fatty acids, synthetic esters of formula $R_1COOR_2$ in which R, represents a $C_{6-29}$ higher fatty acid residue and $R_2$ represents a $C_{3-30}$ hydrocarbon-based chain, and $C_{12-26}$ fatty alcohols, fluoro oils.

These non-volatile oils are preferably present in an amount ranging from 5 to 60% by weight of the total composition. This range includes all specific values and subranges therebetween, such as 10, 15, 20, 25, 30, 40 and 50% by weight of the total composition.

Needless to say, the transfer-resistant cosmetic compositions can also contain active principles which give them their characteristic cosmetic properties and cosmetic adjuvants. These are, for example, substances such as sunscreens, free-radical scavengers, hydrating agents, vitamins, proteins, ceramides, pH regulators, antioxidants, preserving agents, fillers, pigments, dyes, emollients, antifoaming agents, fragrances, surfactants and plasticizers.

Needless to say, a person skilled in the art will take care to select this or these optional additional compounds) and the amount thereof such that the advantageous properties intrinsically associated with the cosmetic composition of the invention are not, or are not substantially, adversely affected.

The composition of the invention preferably contains a particulate phase generally present in a proportion of from 0.05 to 35% of the total weight of the composition, preferably from 2 to 25%, and which can comprise pigments and/or nacres and/or fillers usually used in cosmetic compositions. These ranges include all specific values and subranges therebetween, including 1, 5, 10, 20 and 30% by weight. This filler can give a colored, white or colorless composition.

The term "pigments" refers to white or colored, inorganic or organic particles which are insoluble in the liquid fatty phase and are intended to color and/or opacity the product. The term "fillers" refers to colorless or white, inorganic or synthetic, lamellar or non-lamellar particles. The term "nacres" refers to iridescent particles produced in particular by certain molluscs in their shell, or else synthesized. These fillers and nacres serve in particular to modify the texture of the composition.

The pigments can be present in the composition in a proportion of from 0.05 to 25% of the weight of the final composition, and preferably in a proportion of from 2 to 15%. These ranges include all specific values and subranges therebetween, such as 0.1, 0.2, 0.5, 1, 3, 5, 10, 12, 18 and 20% by weight. As inorganic pigments which can be used in the invention, mention may be made of titanium oxide, zirconium oxide or cerium oxide, as well as zinc oxide, iron oxide or chromium oxide and ferric blue. Among the organic pigments which can be used in the invention, mention may be made of carbon black and barium, strontium, calcium ( DC Red No . 7) and aluminum lakes.

The nacres can be present in the composition in a proportion of from 0 to 20% of the total weight of the composition, preferably in a proportion ranging from 1 to 15%. These ranges include all specific values and subranges therebetween, such as 0.1, 0.2, 0.5, 2, 5, 10 and 15% by weight. Examples of nacres which may be used in the invention include mica coated with titanium oxide, with iron oxide, with natural pigment or with bismuth oxychloride, such as colored titanium mica.

The fillers can be present in a proportion of from 0 to 35% of the total weight of the composition, preferably 2 to 15%. These ranges include all specific values and subranges therebetween, such as 0.1, 0.2, 0.5, 1, 3, 5, 10, 12, 18, 20, 25 and 30% by weight. Mention may be made in particular of talc, mica, silica, kaolin, nylon (in particular Orgasol) powder, polyethylene powder, Teflon, starch, boron nitride, copolymer microspheres such as Expancel (Nobel Industrie), Polytrap (Dow Corning) and silicone resin microbeads (Tospearl from Toshiba, for example).

The compositions of the invention can also contain liposoluble dyes and/or water-soluble dyes.

The cosmetic compositions of the invention can be in a solid, pasty or liquid form. They can be anhydrous compositions or emulsions. Mention may be made, for example, of lipsticks, solid or liquid foundations, mascaras, face powders, eyeshadows and other similar products, concealer products, antisun products, skin-coloring products or body hygiene products (in particular deodorants).

The processes for manufacturing the products according to the invention do not differ in any way from the processes conventionally used in cosmetics and are well-known to those skilled in the art.

A solid cast make-up product such as a lipstick, a solid foundation or a compact powder, may be manufactured, for example, by melting and mixing together the non-volatile components of the composition, adding the volatile phase at a lower temperature, casting the mixture thus obtained in a mould of suitable shape, and cooling to room temperature.

Having generally described this invention, a further understanding can be obtained by reference to certain specific examples which are provided herein for purposes of illustration only and are not intended to be limiting unless otherwise specified.

EXAMPLE 1 (Comparative example)

A lipstick is prepared from the following ingredients:

| | |
|---|---|
| Polyethylene wax sold under the name Performalene 655 ® by New Phase Technologies | 20% by weight |
| Cyclotetradimethylsiloxane (cyclomethicone $D_4$) | 74% by weight |
| DC Red No. 7 calcium lake (pigment) | 6% by weight |

The evaporation speed of the volatile solvent D4 alone is equal to 0.626 mg/cm$^2$/minute under the conditions described in the description.

EXAMPLE 2

A lipstick is prepared from the following ingredients:

| | |
|---|---|
| Polyethylene wax sold under the name Performalene 655 ® by New Phase Technologies | 20% by weight |
| Decamethyltetresiloxane (DC 200 Fluid 1.5 cSt sold by Dow Corning) | 22.2% by weight |
| Isododecane (Permethyl ® 99A sold by Presperse Inc.) | 51.8% by weight |
| DC Red No. 7 calcium lake (pigment) | 6% by weight |

The evaporation speed of the $L_4$/isododecane (3/7) mixture is equal to 0.619 mg/cm$^2$/minute under the conditions described in the description, i.e. barely different from that of cyclomethicone $D_4$ used in Example 1.

EXAMPLE 3

A lipstick is prepared from the following ingredients:

| | |
|---|---|
| Polyethylene wax sold under the name Performalene GS53 by New Phase Technologies | 20% by weight |
| Decamethyltetrasiloxane (DC 200 Fluid 1.5 cSt sold by Dow Corning) | 66.6% by weight |

| | |
|---|---|
| Mixture of isoparaffins (Isopar E ® sold by Exxon Chemical) | 7.4% by weight |
| DC Red No. 7 calcium lake (pigment) | 6% by weight |

The evaporation speed of the $L_4$/isoparaffins (¾) volatile mixture is equal to 0.926 mg/cm²/minute under the conditions described in the description. The order of magnitude in Example 1 is found.

The lipsticks of Examples 2 and 3 do not crystallize when stored at low temperature.

Obviously, numerous modifications and variations of the present invention are possible in light of the above teachings. It is therefore to be understood that within the scope of the appended claims, the invention may be practiced otherwise than as specifically described herein.

This Application is based on French Patent Application Serial Nos. 98-10256 and 98-11065, filed on Aug. 10, 1998 and Sep. 4, 1998, both of which are incorporated herein by reference in their entirety.

What is claimed is:

1. A transfer-resistant make-up or care composition comprising:
   a fatty phase, and
   a volatile solvent consisting essentially of a linear decamethyltetrasiloxane and at least one additional solvent which has an evaporation speed that is greater than the evaporation speed of the linear decamethyltetrasiloxane.

2. The transfer-resistant composition of claim 1, wherein the additional solvent is selected from the group consisting of linear or branched alkanes, cycloalkanes fluorohydrocarbons, silicones, modified silicones, and mixtures thereof.

3. The transfer-resistant composition of claim 1, wherein the volatile solvent comprises 15 to 40% by weight of the decamethyltetrasiloxane, and the ratio of the evaporation speed of the additional solvent to evaporation speed of the decamethyltetrasiloxane is 2.2 to 3.

4. The transfer-resistant composition of claim 1, wherein the volatile solvent comprises 25 to 35% by weight of the decamethyltetrasiloxane, and the ratio of the evaporation speed of the additional solvent to evaporation speed of the decamethyltetrasiloxane is 2.4 to 2.8.

5. The transfer-resistant composition of claim 1, wherein the volatile solvent comprises 75 to 95% by weight of the decamethyltetrasiloxane, and the ratio of the evaporation speed of the additional solvent to evaporation speed of the decamethyltetrasiloxane is 12.9 to 22.7.

6. The transfer-resistant composition of claim 1, wherein the volatile solvent comprises 85 to 95% by weight of the decamethyltetrasiloxane, and the ratio of the evaporation speed of the additional solvent to evaporation speed of the decamethyltetrasiloxane is 16.1 to 19.5.

7. The transfer-resistant composition of claim 1, wherein the additional solvent is isododecane (2,2,4,4,6-pentamethylheptane), a mixture of isoparaffins, octamethyltrisiloxane, hexamethyldisiloxane, or a mixture thereof.

8. The transfer-resistant composition of claim 7, wherein the additional solvent is octamethyltrisiloxane, and the weight ratio of the octamethyltrisiloxane to the decamethyltetrasiloxane is less than 0.4.

9. The transfer-resistant composition of claim 1, wherein the additional solvent is a mixture of at least two solvents.

10. The transfer-resistant composition of claim 9, wherein the additional solvent is a mixture of isododecane and at least one volatile silicone selected from the group consisting of octamethyltrisiloxane and hexamethyldisiloxane.

11. The transfer-resistant composition of claim 10, wherein the additional solvent is a mixture of isododecane and octamethyltrisiloxane, and the octamethyltrisiloxane/decamethyltetrasiloxane ratio is less than 0.4.

12. The transfer-resistant composition of claim 1, further comprising one or more waxes of animal, plant or synthetic origin.

13. The transfer-resistant composition of claim 1, further comprising a silicone gum.

14. The transfer-resistant composition of claim 13, comprising less than 2% by weight of the silicone gum.

15. The transfer-resistant composition of claim 1, further comprising at least one non-volatile oil of plant, animal, mineral or synthetic origin.

16. The transfer-resistant composition of claim 15, comprising 5 and 60% by weight of the non-volatile oil.

17. The transfer-resistant composition of claim 1, further comprising one or more cosmetic active agents or adjuvants selected from the group consisting of sunscreens, free-radical scavengers, hydrating agents, vitamins, proteins, ceramides, pH regulators, antioxidants, preserving agents, pigments, dyes, emollients, antifoaming agents, silicones, fragrances, surfactants, plasticizers, and mixtures thereof.

18. The transfer-resistant composition of claim 1, which is in the form of a solid, liquid or pasty make-up product, which is in anhydrous or emulsion form.

19. The transfer-resistant composition of claim 18, which is in the form of a solid make-up product.

20. The transfer-resistant composition of claim 18, wherein the make-up product is a lipstick, a foundation, a face powder, an eyeshadow or a mascara.

21. A method of preparing the composition of claim 1, comprising combining the fatty phase and the volatile solvent.

22. A method of increasing the transfer resistance of make-up or care compositions for the skin, comprising incorporating the composition of claim 1 into a make-up or care composition for the skin.

* * * * *